United States Patent [19]

Gaillard

[11] 4,401,559

[45] Aug. 30, 1983

[54] PROCESS FOR REMOVING HALOGENATED IMPURITIES FROM OLEFIN OLIGOMERS

[75] Inventor: Jean Gaillard, Lyon, France

[73] Assignee: Institut Francais du Petrole, Rueil-Malmaison, France

[21] Appl. No.: 370,237

[22] Filed: Apr. 21, 1982

[30] Foreign Application Priority Data

Apr. 21, 1981 [FR] France ................... 81 08078

[51] Int. Cl.³ ............................................. C10G 17/04
[52] U.S. Cl. ................................. 208/262; 585/856; 585/860
[58] Field of Search ............... 585/856, 862, 864, 860; 208/262

[56] References Cited

U.S. PATENT DOCUMENTS 2,908,730  10/1959  Binning et al. ............... 585/860
3,394,078  7/1968  Peurifoy et al. ............... 208/262

Primary Examiner—Delbert E. Gantz
Assistant Examiner—Anthony McFarlane
Attorney, Agent, or Firm—Millen & White

[57] ABSTRACT

Process for removing halogenated impurities from olefin oligomers by extraction with a polar solvent such as dimethylsulfoxide, acetonitrile, dimethylacetamide, dimethylformamide, diethylene glycol or dimethylsulfone.

5 Claims, No Drawings

PROCESS FOR REMOVING HALOGENATED IMPURITIES FROM OLEFIN OLIGOMERS

BACKGROUND OF THE INVENTION

The object of the present invention is a process for removing halogenated impurities from olefins.

French Pat. No. 2 443 877 discloses an improved catalytic composition and its use as an oligomerization catalyst for monoolefins, for example those having from 2 to 4 carbon atoms and particularly as a dimerization and/or trimerization catalyst therefor. This catalytic composition consists of the product obtained by contacting, in any order, a bivalent nickel compound with a hydrocarbyl aluminum halide and an organic Bronsted acid, preferably a halogenocarboxylic acid, for example trichloracetic acid or trifluoracetic acid. However an additional problem has appeared: all or part of the halogen is found in the resultant olefinic oligomerizate, which is unacceptable for a number of uses of this oligomerizate. The difficulty of removing the traces of halogen was then encountered. In view of the acidic nature of the halogenated compounds introduced into the catalyst, it could be expected that washing the oligomerizate with water or with a base in aqueous medium would remove these traces of halogen. The failure of this method shows that the problem has no obvious solution and that the halogen is probably engaged in the form of a compound soluble in hydrocarbons and which cannot be extracted easily.

SUMMARY

It has surprisingly been found that these compounds can be removed by extraction with a polar solvent substantially immiscible with the olefins. The preferred solvents are dimethylsulfoxide, acetonitrile, dimethylacetamide, dimethylformamide, diethylene glycol, dimethylsulfone, their mixtures and their mixtures with water. More generally a polar solvent is an organic compound used in liquid phase, the molecule of which comprises carbon, hydrogen and at least one heteroelement such as oxygen, sulfur, nitrogen and/or phosphorus.

The invention is not limited to the treatment of a mixture of olefins obtained by oligomerization. It applies in all cases where a hydrocarbon contains, in solution, a halogenated compound not extractable with water or with an aqueous base.

According to the invention, the olefins mixture, containing halogenated hydrocarbons, is treated with the polar solvent or the mixture of several polar solvents in one step or with repeated extraction steps. A continuous operation can also be conducted in a counter-current extraction column. The proportion of the polar solvent is, for example, from 0.01 to 10 parts by weight per part of olefins. The extraction is conducted by intimate mixing of the two phases by efficient stirring or in an extraction column, then decantation and withdrawing of the polar phase. In certain cases, traces of polar solvent can remain dissolved in the hydrocarbons phase; they can be removed easily by water-washing.

The extraction solvent, containing the halogenated compound, can be used again after distillation.

EXAMPLES

The following examples illustrate the invention without limiting the scope therefore.

EXAMPLE 1

The oligomerization of a halogen-free butenes fraction, by means of a catalytic system formed by reacting nickel heptanoate with dichloroethylaluminum and trifluoracetic acid has lead to an oligomers mixture whose trimer fraction contains 250 parts per million by weight of fluorine. 100 ml of this fraction are treated three times at 20° C. with 30 ml of dimethylsulfoxide. After treatment, the trimer fraction contains only 15 parts per million of fluorine.

EXAMPLE 2

100 ml of the same olefins mixture as used in example 1 are treated three times with 30 ml of acetonitrile. After treatment, the olefins mixture contains only 25 parts per million of fluorine.

EXAMPLE 3

Example 2 has been repeated, except that the acetonitrile contained 5% b.w. of water. After treatment, the mixture contained only 18 parts per million of fluorine.

What is claimed is:

1. A liquid-liquid solvent extraction process for removing fluorine-containing compounds from an olefinic cut resulting from dimerizing or trimerizing at least one monoolefin having from 2 to 4 carbon atoms in the presence of a catalyst obtained by contacting a bivalent nickel compound with a hydrocarbyl aluminum halide and a trifluoroacetic acid, said process consisting essentially of intimately mixing said olefinic cut with an immiscible liquid phase of polar organic solvent selected from dimethylsulfoxide, acetonitrile, dimethylacetamide, dimethylformamide, diethylene glycol, dimethylsulfone, their mixtures and their mixtures with water, the proportion of polar organic solvent being from 0.01 to 10 parts by weight per part by weight of olefinic cut, to transfer said fluorine-containing compounds to said immiscible phase, and separating resultant purified liquid olefinic cut from said immiscible phase.

2. A process according to claim 1, further comprising distilling resultant immiscible liquid to remove said fluorine-containing compounds therefrom, and reusing resultant purified immiscible phase in said solvent extraction process.

3. A process according to claim 1, wherein said polar organic solvent is dimethyl sulfoxide.

4. A process according to claim 1, wherein said polar organic solvent is acetonitrile.

5. A process according to claim 4, wherein said immiscible liquid phase contains about 95% acetonitrile and 5% water.

* * * * *